(12) United States Patent
Roth

(10) Patent No.: US 7,966,864 B2
(45) Date of Patent: Jun. 28, 2011

(54) METHOD FOR ASCERTAINING AN ETHANOL CONTENT OF A FUEL

(75) Inventor: Peter Roth, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 383 days.

(21) Appl. No.: 12/206,466

(22) Filed: Sep. 8, 2008

(65) Prior Publication Data
US 2009/0064767 A1 Mar. 12, 2009

(30) Foreign Application Priority Data

Sep. 10, 2007 (DE) .......................... 10 2007 042 992

(51) Int. Cl.
*G01N 33/00* (2006.01)
*G01N 7/00* (2006.01)

(52) U.S. Cl. ...................................... 73/61.43; 73/64.45

(58) Field of Classification Search ................. 73/61.43, 73/61.46, 61.47, 64.45
See application file for complete search history.

(56) References Cited

U.S. PATENT DOCUMENTS
3,056,282 A * 10/1962 Boyd, Jr. ....................... 73/61.76
6,755,183 B2 * 6/2004 Frech et al. .................... 123/491

OTHER PUBLICATIONS

Pumphrey, J.A. et al. "Vapor pressure measurements and predictions for alcohol-gasoline blends"; Fuel, vol. 79, No. 11, Sep. 2000, pp. 1405-1411.

* cited by examiner

*Primary Examiner* — Hezron Williams
*Assistant Examiner* — Nathaniel Kolb
(74) *Attorney, Agent, or Firm* — Merchant & Gould P.C.

(57) ABSTRACT

Method for ascertaining an ethanol content of a fuel with the steps: ascertaining the vapor pressure of the fuel, ascertaining the temperature of the fuel and ascertaining the ethanol content of the fuel as a function of the vapor pressure and the temperature, which were ascertained.

8 Claims, 2 Drawing Sheets

METHOD FOR ASCERTAINING AN ETHANOL CONTENT OF A FUEL

TECHNICAL FIELD

The invention at hand relates to a method and a device for ascertaining an ethanol content of a fuel.

BACKGROUND

In order to provide an alternative to petroleum based fuels, ethanol or a blend of gasoline and ethanol is increasingly being used to drive internal combustion engines of motor vehicles. So-called flex fuel vehicles, which can be driven with fuels containing ethanol in addition to gasoline, are particularly practical for the driver of a motor vehicle. The ethanol content of said fuels usually varies between 0% and 85%. The challenge, which thereby arises, is that the internal combustion engine is driven according to the prevailing fuel in use. It must thereby be taken into account that gasoline and ethanol have a different combustion behavior. That is why the ethanol content in the fuel has to be determined as exactly as possible in order for an optimal knock control, an ignition at the ideal point in time, an injection with the correct air/fuel mixture etc. to take place.

The following conventional methods are known from the technical field.

A known method provides for an ethanol content sensor to be used, which ascertains the ethanol content of the fuel present in a fuel tank and supplies a corresponding signal to the control system of the internal combustion engine.

Another method goes without this additional ethanol content sensor and instead uses the fact that the stoichiometric air requirement is a function of the ethanol content. Provision is thus made in this method for the closed-loop lambda control to be monitored after a filling of the tank (fueling) has been detected. The ethanol content of the fuel is then suggested as a function of the deviation of the closed-loop lambda control from a map-based pilot control.

A disadvantage of the technical field is that the method, which was first mentioned, requires an additional ethanol content sensor and that the second method depends upon the closed-loop lambda control not being disrupted by other influencing factors. It is, therefore, questionable whether a lambda deviation, which was detected in the closed-loop lambda control, can actually be attributed to an altered ethanol content in the fuel or whether in fact tolerances in the system or air conditions, which have changed, are responsible for the deviation in the closed-loop lambda control.

SUMMARY

It is a task of the invention to state an improved method and an improved device, with which the ethanol content in the fuel can be better ascertained, i.e. particularly with regard to accuracy or reduction of costs. In general it is the task of the invention to improve the methods and devices from the technical field, which are described above.

This problem is solved by a method for ascertaining an ethanol content of a fuel with the following steps: ascertaining the vapor pressure of the fuel, ascertaining the temperature of the fuel and ascertaining the ethanol content of the fuel as a function of the vapor pressure and the temperature, which were previously ascertained.

Provision is made within the scope of the invention for known or experimentally ascertained tables or functions to be used in order to determine the ethanol content of the fuel from the temperature of the fuel and the vapor pressure of the fuel, which were ascertained. In so doing, the temperature can be ascertained, in that it is directly measured, for example by an already existing sensor or in that it is derived from other variables through calculation.

The fuel is preferably pumped out of a low pressure system by a pump. The pump extracts the fuel from the low pressure system, and in so doing, the vapor pressure is ascertained, in that the pressure is lowered in the low pressure system up until the delivery rate of the pump drops. The reason behind this step is that when the pressure is lowered in the low pressure system at the same time the vapor pressure of the fuel is high, the pump is no longer adequately provided with liquid fuel when a comparatively small drop in the pressure of the low pressure system occurs, but in fact is already pumping gaseous fuel. As soon as the pump pumps just a small percentage of gaseous fuel, the delivery rate of the pump is noticeably reduced. The pressure, at which the delivery rate of the pump drops, can thus be used as an indicator for the vapor pressure of the fuel.

The pressure is advantageously raised again in the low pressure system immediately after a drop in the delivery rate of the pump has been detected. This provides the advantage that the fuel supply of the internal combustion engine, which is supplied with fuel by the pump, is only slightly affected; and the effect is of no consequence for the operation of the internal combustion engine.

A drop in the delivery rate is preferably detected if the delivery rate falls below a certain threshold value. The delivery rate of the pump is continuously subjected to small fluctuations, for example due to the fluctuations in the voltage of the vehicle's electrical system. Therefore, faulty measurements are avoided by the use of a threshold value.

The pump is advantageously a high pressure pump, which pumps the fuel out of the low pressure system into a high pressure system. This is advantageous in that an interruption of the fuel supply does not occur when the delivery rate drops, because fuel is continuously stored in the high pressure system.

The drop in the delivery rate of the high pressure pump is advantageously acquired on the basis of the pressure in the high pressure system. The pressure in the high pressure system reacts very sensitively and quickly to a drop in the delivery rate of the high pressure pump, so that in this way a drop in the delivery rate of the high pressure pump can be quickly acquired. Furthermore, this characteristic is advantageous because the pressure in the high pressure system is already monitored, so that no additional sensors are necessary.

The threshold value is advantageously a pressure threshold value for the pressure in the high pressure system. This is advantageous, in that smaller fluctuations in the pressure in the high pressure system do not lead to a mistaken assumption of a drop in the delivery rate.

The method is preferably suited to the purpose of ascertaining the ethanol content of a fuel, which essentially consists of gasoline and ethanol. It has become apparent within the scope of the invention that particularly a blend of gasoline and ethanol can be detected and analyzed in the manner described above.

An independent subject matter of the invention is a device, particularly a control unit for the fuel supply of an internal combustion engine, for ascertaining an ethanol content of a fuel, whereby the device for implementing the method according to the invention, which is mentioned above, is equipped with one or a plurality of the preferred characteristics, which are mentioned above.

An additional independent subject matter of the invention is a computer program with a program code for implementing all of the steps of such a method if the program is executed on a computer.

BRIEF DESCRIPTION OF THE DRAWINGS

An example of embodiment of the invention at hand is explained below in detail with the aid of the accompanying drawings. The following are shown.

DETAILED DESCRIPTION

Figure 1:
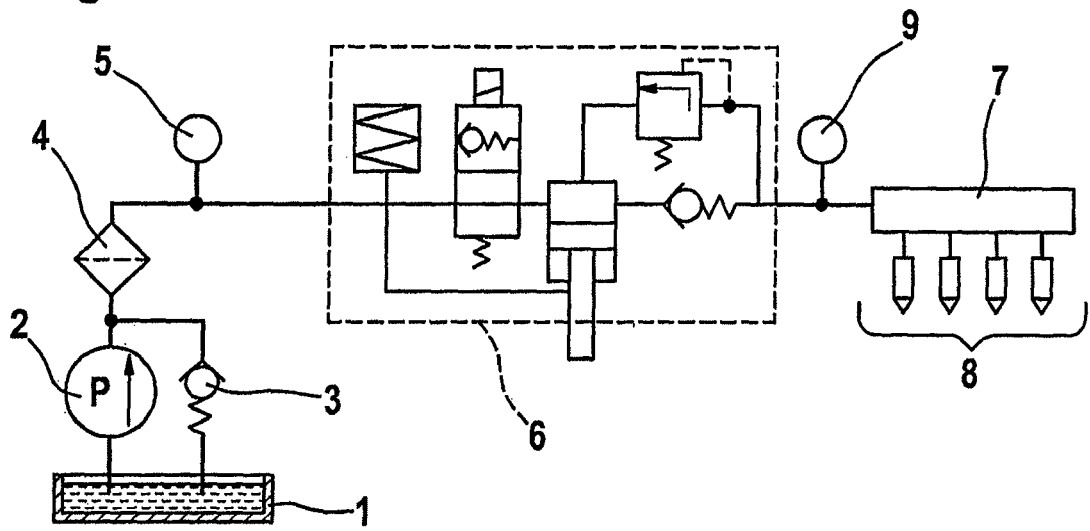
FIG. 1 is an outline of a fuel supply system, wherein the invention can be executed.

A fuel supply system for direct gasoline injection is shown in FIG. 1, wherein the following components are schematically depicted in detail. The fuel is stored in a tank 1, from which it is extracted by a pre-conveying pump or a low pressure pump 2. Provision is made for a pressure-relief valve 3 in order to limit the pressure downstream from the low pressure pump 2. In addition a fuel filter 4 is disposed downstream from the low pressure pump 2. The pressure in the low pressure system is in turn acquired by a low pressure sensor 5 downstream from the fuel filter 4. A high pressure pump 6 is provided with fuel from the low pressure system. Said high pressure pump 6 in turn supplies the injectors with fuel via a high pressure system with common rail 7. The pressure in the high pressure system is acquired by a high pressure sensor 9.

Figure 2:
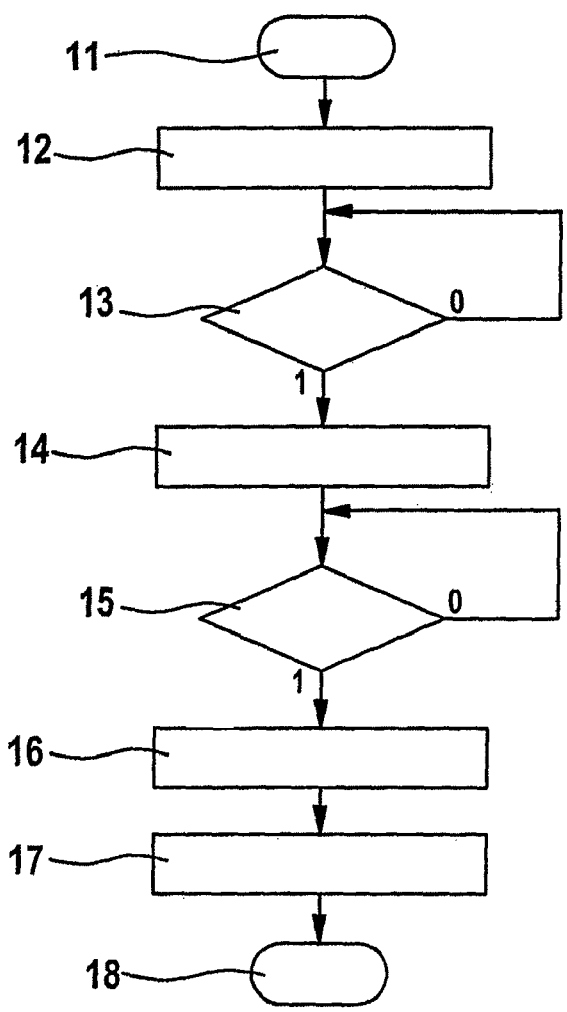
FIG. 2 is a schematic diagram of the execution of a method according to the invention.

A method according to the invention is described below in conjunction with FIG. 2, wherein reference is made to the description of FIG. 1 and like reference numerals designate like parts.

The method for ascertaining the ethanol content of the fuel in the fuel tank 1 begins with step 11, if the operation of the internal combustion engine, which is supplied by the injectors 8 with fuel, is resumed after a filling of the tank (fueling). The temperature of the fuel in the low pressure system is initially estimated; and in so doing, the temperature measured by a temperature sensor in the fuel tank 1 is used as an estimated value for the temperature. A test is subsequently made in step 13 to determine whether essentially steady state operating conditions for introducing a vapor pressure measurement prevail. A test is thereby made of the following operating conditions: An essentially constant pressure in the low pressure system and an essentially constant pressure in the high pressure system.

As long as no operating conditions, which are approximately constant, are detected, the method pauses in step 13. In the event in step 13, essentially constant operating conditions are detected with respect to the pressure values previously mentioned, the method begins in step 14 to lower the pressure in the low pressure system by reducing the delivery rate of the low pressure pump 2. The method then waits to see whether the high pressure sensor 9 detects a drop in the pressure in the high pressure system under a certain threshold value. As long as the high pressure sensor does not detect such a drop, the method pauses in step 15. During the pause in step 15, the pressure in the low pressure system is continuously lowered. As soon as a drop in pressure in the high pressure system is detected in step 15, the method proceeds with step 16, wherein an inquiry is made about the pressure in the low pressure system with the aid of the low pressure sensor 5. This pressure is used as the value for the vapor pressure of the fuel. Subsequently in step 17, it is ascertained on the basis of a table, which ethanol content can be assigned to the temperature of the fuel and the vapor pressure of the fuel, which were ascertained. This table is stored in a control system for the method. The method ends in step 18.

Figure 3:
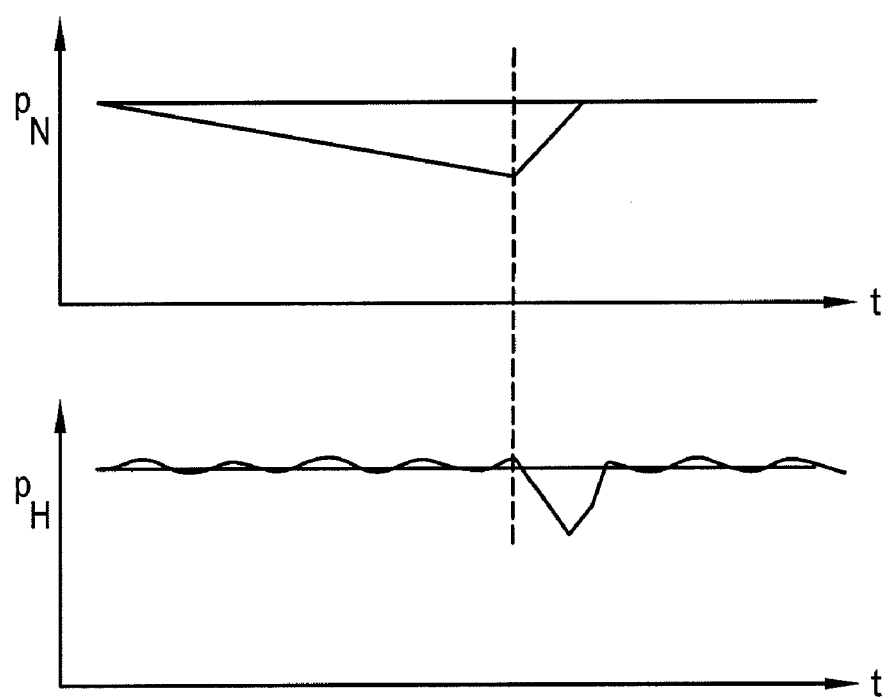
FIG. 3 is a pressure history at two different positions in the fuel supply system of FIG. 1 during execution of the method according to the invention outlined in FIG. 2.

In FIG. 3, the pressure history in the low pressure system ($p_N$) and the pressure history in the high pressure system ($p_H$) are exemplary depicted versus time (t). The diagrams begin corresponding to step 14 with a drop in pressure in the low pressure system $p_N$. Subsequently the pressure in the low pressure system $p_N$ drops continuously. In the meantime, the pressure initially remains essentially constant in the high pressure system $p_H$ and fluctuates only slightly due to the operation of the injectors and the internal combustion engine. A drop in the pressure in the high pressure system $p_H$ below the nominal minimum pressure is however detected at the time indicated with a dashed line. This corresponds in the method of FIG. 2 to the transition from step 15 to step 16. The low pressure pump 2 is subsequently set into operation, so that the pressure in the low pressure system $p_N$ increases again. The pressure in the high pressure system $p_H$ initially still drops for a short period of time before it too again increases due to the restoration of the delivery rate of the high pressure pump 6.

The invention claimed is:

1. A method of ascertaining an ethanol content of a fuel, the method comprising:
    ascertaining a vapor pressure of the fuel by pumping the fuel out of a low pressure system wherein a pressure in the low pressure system is decreased until a drop in a delivery rate of the pump occurs; and
    ascertaining a temperature of the fuel;
    wherein the ethanol content of the fuel is ascertained as a function of the ascertained vapor pressure and temperature.

2. A method according to claim 1, further comprising raising the pressure in the low pressure system immediately after a detection of the drop in the delivery rate of the pump.

3. A method according to claim 2, wherein a drop in the delivery rate is detected if the delivery rate of the pump drops below a threshold value.

4. A method according to claim 1, wherein the pump is a high pressure pump that pumps the fuel out of the low pressure system into a high pressure system.

5. A method according to claim 4, further comprising acquiring the drop in the delivery rate of the pump on a basis of a pressure in the high pressure system.

6. A method according to claim 5, wherein the threshold value is a pressure threshold value for the pressure in the high pressure system.

7. A method according to claim 1, further comprising ascertaining the ethanol content of a fuel consisting of an ethanol and a gasoline component.

8. A non-transitory computer-readable medium containing a program code to implement, if executed on a computer, a method of ascertaining an ethanol content of a fuel, the method comprising:
    ascertaining a vapor pressure of the fuel by pumping the fuel out of a low pressure system wherein a pressure in the low pressure system is decreased until a drop in a delivery rate of the pump occurs; and
    ascertaining a temperature of the fuel;
    wherein the ethanol content of the fuel is ascertained as a function of the ascertained vapor pressure and temperature.

* * * * *